United States Patent
Souzy et al.

(10) Patent No.: US 11,253,223 B2
(45) Date of Patent: Feb. 22, 2022

(54) ULTRASONIC METHOD AND APPARATUS FOR RESPIRATION MONITORING

(71) Applicant: RESPINOR AS, Oslo (NO)

(72) Inventors: Nicolas Souzy, Oslo (NO); Morten Eriksen, Oslo (NO); Nicolay Berard-Andersen, Oslo (NO)

(73) Assignee: Respinor AS, Oslo (NO)

(*) Notice: Subject to any disclaimer, the term of this patent is extended or adjusted under 35 U.S.C. 154(b) by 601 days.

(21) Appl. No.: 15/977,603

(22) Filed: May 11, 2018

(65) Prior Publication Data

US 2018/0256075 A1 Sep. 13, 2018

Related U.S. Application Data

(63) Continuation-in-part of application No. PCT/EP2016/077426, filed on Nov. 11, 2016.

(30) Foreign Application Priority Data

Nov. 12, 2015 (GB) .................................. 1519985
Aug. 30, 2016 (GB) .................................. 1614633

(51) Int. Cl.
*A61B 8/08* (2006.01)
*A61B 8/00* (2006.01)
(Continued)

(52) U.S. Cl.
CPC .................. *A61B 8/08* (2013.01); *A61B 5/08* (2013.01); *A61B 5/0816* (2013.01); *A61B 5/113* (2013.01);
(Continued)

(58) Field of Classification Search
CPC ......... A61B 8/5223; A61B 8/08; A61B 8/085; A61B 5/113; A61B 5/08; A61B 5/0816;
(Continued)

(56) References Cited

U.S. PATENT DOCUMENTS 4,122,427 A 10/1978 Karsh
4,573,477 A 3/1986 Namekawa et al.
(Continued)

FOREIGN PATENT DOCUMENTS

CN 101198434 A 6/2008
CN 102192769 A 9/2011
(Continued)

OTHER PUBLICATIONS

Grams et al. Assessment of the reproducibility of the indirect ultrasound method of measuring diaphragm mobility. Clinical Physiology and Functional Imaging. Jan. 2014;34(1):18-25 (Year: 2014).*
(Continued)

*Primary Examiner* — Serkan Akar
*Assistant Examiner* — Helene Bor
(74) *Attorney, Agent, or Firm* — Sterne, Kessler, Goldstein & Fox P.L.L.C.

(57) ABSTRACT

A method of non-invasively monitoring the respiration of a patient comprises: transmitting ultrasound into the body toward an internal structure of the patient's body, the internal structure being one of the liver, the spleen or a kidney; selecting a depth range; measuring the phase of ultrasound echo signals from the internal structure at multiple points along the depth range for at least a first and a second echo signal, the first and second echo signals being received at different times; detecting the motion of the internal structure within the patient's abdomen by reference to differences in the measured phase between the first and the second echo signals; and thereby monitoring the respiration of the patient by associating movement of the internal structure with movement caused by respiration.

33 Claims, 7 Drawing Sheets

(51) Int. Cl.
   *A61B 5/00* (2006.01)
   *A61B 5/113* (2006.01)
   *A61B 5/08* (2006.01)

(52) U.S. Cl.
   CPC .......... *A61B 5/1135* (2013.01); *A61B 5/6823* (2013.01); *A61B 5/6832* (2013.01); *A61B 8/00* (2013.01); *A61B 8/085* (2013.01); *A61B 8/4236* (2013.01); *A61B 8/4281* (2013.01); *A61B 8/5207* (2013.01); *A61B 8/4427* (2013.01); *A61B 8/488* (2013.01)

(58) Field of Classification Search
   CPC ....... A61B 8/00; A61B 5/1135; G01S 13/582; G01S 13/583; G01S 13/581
   See application file for complete search history.

(56) References Cited

U.S. PATENT DOCUMENTS

| | | | |
|---|---|---|---|
| 5,088,498 A * | 2/1992 | Beach et al. | |
| 5,111,825 A * | 5/1992 | Nishiyama | |
| 5,573,012 A * | 11/1996 | McEwan ................ | A61B 5/024 600/428 |
| 6,314,312 B1 * | 11/2001 | Wessels ................ | A61B 90/10 600/427 |
| 8,498,828 B2 | 7/2013 | Sasaki | |
| 10,098,572 B2 | 10/2018 | Schwenk et al. | |
| 10,207,072 B2 | 2/2019 | Dunn et al. | |
| 10,271,739 B2 | 4/2019 | Freeman et al. | |
| 2002/0115923 A1 * | 8/2002 | Erbel ................... | A61B 6/541 600/407 |
| 2004/0167389 A1 * | 8/2004 | Brabrand | |
| 2004/0242997 A1 | 12/2004 | Griffin et al. | |
| 2006/0079782 A1 * | 4/2006 | Beach et al. | |
| 2006/0285071 A1 | 12/2006 | Erickson et al. | |
| 2009/0048518 A1 * | 2/2009 | Furnam et al. | |
| 2010/0076315 A1 | 3/2010 | Erkamp et al. | |
| 2010/0081929 A1 | 4/2010 | Suzuki | |
| 2011/0121996 A1 | 5/2011 | Griffin et al. | |
| 2011/0208060 A1 | 8/2011 | Haase et al. | |
| 2013/0030285 A1 | 1/2013 | Vaillant et al. | |
| 2013/0079628 A1 | 3/2013 | Groszmann et al. | |
| 2013/0165005 A1 | 6/2013 | Berard-Andersen et al. | |
| 2014/0213902 A1 * | 7/2014 | Nagae et al. | |
| 2014/0233794 A1 | 8/2014 | Oh et al. | |
| 2015/0223782 A1 | 8/2015 | Yamagata et al. | |
| 2015/0238169 A1 | 8/2015 | Mizukami | |
| 2016/0000409 A1 * | 1/2016 | Bruder et al. | |
| 2021/0038119 A1 | 2/2021 | Souzy et al. | |

FOREIGN PATENT DOCUMENTS

| | | |
|---|---|---|
| CN | 102469957 A | 5/2012 |
| CN | 103584847 A | 2/2014 |
| CN | 103930168 A | 7/2014 |
| CN | 103948401 A | 7/2014 |
| CN | 104703548 A | 6/2015 |
| CN | 104840218 A | 8/2015 |
| CN | 104873224 A | 9/2015 |
| GB | 2 443 43 3 A | 5/2008 |
| JP | S 62-044494 B2 | 9/1987 |
| JP | H 05-168633 A | 7/1993 |
| JP | 2010-504829 A | 2/2010 |
| JP | 2014-502854 A | 2/2014 |
| WO | WO 94/20021 A2 | 9/1994 |
| WO | WO 2004/049951 A1 | 6/2004 |
| WO | WO 2005/007200 A1 | 1/2005 |
| WO | WO 2006/057911 A2 | 6/2006 |
| WO | WO 2007/032329 A1 | 3/2007 |
| WO | WO 2010/052476 A1 | 5/2010 |
| WO | WO 2011/135288 A2 | 11/2011 |
| WO | WO 2012/142031 A1 | 10/2012 |
| WO | WO 2014/111860 A2 | 7/2014 |

OTHER PUBLICATIONS

International Search Report and Written Opinion directed to related International Patent Application No. PCT/EP2016/077426, dated Feb. 3, 2017; 10 pages.

Wein et al., 'Ultrasound based respiratory motion compensation in the abdomen' 2008 Workshop on Image Guidance and Computer Assistance for Soft Tissue Interventions. vol. 32, No. 294, pp. 1-8.

\* cited by examiner

ULTRASONIC METHOD AND APPARATUS FOR RESPIRATION MONITORING

CROSS-REFERENCE TO RELATED APPLICATIONS

This application is a continuation-in-part of International Application No. PCT/EP2016/077426, filed on Nov. 11, 2016, which claims priority to Great Britain Application No. 1614633.4, filed Aug. 30, 2016 and to Great Britain Application No. 1519985.4, filed on Nov. 12, 2015, the disclosures of which are incorporated herein in their entireties.

FIELD

The present invention relates to a non-invasive method and apparatus for monitoring the respiration of a medical or surgical patient, in particularly using ultrasound.

BACKGROUND

Measurement and monitoring of respiration is essential to treatment of a wide range of medical conditions where mistakes have grave consequences for the patients and are associated with considerable economic cost for the society. The thoracic diaphragm is the main breathing muscle, and its dysfunction can be symptomatic of many respiratory disorders and conditions.

WO 2004/049951 discloses a respiration monitor comprising an ultrasound transducer array having a plurality of individual transducer elements positioned in an intercostal space so as to span at least part of the region of thoracic diaphragm movement of a patient. Because air has a much lower acoustic impedance than tissue, the reflection of the ultrasound beam is much more pronounced when the lung is insonated. By measuring the strength of the receiving signal, it is possible to determine the presence of the patient's lung, and hence the degree of inspiration by using several transducers located along the direction of the motion of the lower lung border.

In accordance with another existing technique, the motion of the diaphragm can instead be measured by conventional ultrasound imaging techniques. A beam of ultrasound pulses is aimed from a transducer onto the skin surface towards the diaphragm from below, via the liver. A distinct, strong echo can then be detected from the diaphragm since it is a smooth, specular surface. The variations in the distance between the ultrasound transducer and this echo can then be used for measuring the magnitude of the excursions. Instead of using only a narrow beam (M-mode), a real-time two-dimensional ultrasound image (B-mode) might also be used, with the additional advantage of securing a better anatomical orientation.

SUMMARY

It is desirable to provide further methods for monitoring of respiration.

The present invention provides a method of non-invasively monitoring the respiration of a patient comprising: transmitting ultrasound into the body toward an internal structure of the patient's body, the internal structure being one of the liver, the spleen or a kidney; selecting a depth range; measuring the phase of ultrasound echo signals from the internal structure at multiple points along the depth range for at least a first and a second echo signal, the first and second echo signals being received at different times; detecting the motion of the internal structure within the patient's abdomen by reference to differences in the measured phase between the first and the second echo signals; and thereby monitoring the respiration of the patient by associating movement of the internal structure with movement caused by respiration.

It has been found that movement of the internal structures closely mirrors movement caused by respiration, such as movements of the thoracic diaphragm, which in turn can be used to monitor the respiration of a patient. The diaphragm is the major muscle of inspiration, and continuous monitoring may support and add information to decision makers in a variety of settings therefore making it a "technology platform" for applications in respiratory diseases, and operating room to emergency room settings. Surprisingly, the movement of internal structures as in the first aspect can be reliably mapped to the patient's respiration. The depth range may be selected based on the internal structure of interest and/or based on prior assessment of the patient, including earlier non-invasive imaging, for example. For the liver a depth range of 2-5 cm may be selected. The depth range is selected to cover a sufficient section of the internal structure so that if for some reason the signal from a part of the range is weak, as might happen if the beam is aimed through a low echo region such as a blood vessel or a bile duct, then there will always be neighbouring tissue regions within the range with adequate echo intensity that can be used instead.

The internal structures of interest are composed of generally solid tissue and move generally as a solid body. They are not liquid or gas filled such as blood vessels, the gallbladder or intestines. They are further of a sufficient size that movement caused by respiration does not cause the tissue to move entirely out of a field of view. Ultrasound is non-invasive, effective and can be used for prolonged periods of time without harm to the patient. Thus, for example, a transducer could remain on the patient for hours, days or even weeks if necessary, while continuously monitoring respiration.

The size of the ultrasound sample volume along the beam direction is preferably in the range from 2 to 5 cm. This will improve the amplitude stability of the signal and avoid drop-outs where a smaller sample volume might happen to be completely inside a vessel or a bile duct.

The method may use an unfocused, or only slightly focused, ultrasound beam. Doing so increases the time of observation of individual scatter elements in the tissue when motion is in a direction that deviates from the direction of the sound beam, and will improve the accuracy of the estimated motion and velocity.

The motion of the internal structure is calculated based on the measured phase at the multiple points along the depth range and the differences in phase for at least two echo signals received at different times. This may be implemented by calculating the displacement of the tissue as an average along the ultrasound sound beam, where the observations of displacement at the multiple points along the depth range are weighted by their signal intensities before the averaged displacement is calculated. Note that in this situation the displacement is directly related to the phase and hence the phase difference can be considered as analogous to a displacement difference. The measured phases are monitored over time in order to identify the difference in phase with time between at least the first and second echo signal at different points on the depth range. The first and second echo signals may be consecutive signals or they may be spaced apart by other echo signals. The difference in phase with time may be determined over more than two echo signals.

The multiple points along the depth range include at least two points providing an echo signal of sufficient strength, for example a strength over a given threshold. Three or more points may be used. It should be understood that the term "point" could in certain circumstances be construed as a short distance or range along the depth range. The method may comprise using interferometry to determine a phase of a returned ultrasound echo and cumulatively summing the phase shift between ultrasound measurements at different depths to determine a displacement of the structure.

The method may comprise determining a phase shift caused by motion at two or more locations along the depth range within the tissue and determining an average phase shift to determine the motion. Doing so will determine the motion with improved accuracy. The multiple locations may be independently measured using two or more transducers, or may be measured at different depths of an ultrasound beam from a single transducer. The average is preferably an intensity-weighted average of the multiple measurements as explained above. Solid tissue, such as the liver, has structural irregularities that scatter ultrasound and the echo received from the tissue will be a sum of individual contributions from such scattering elements. Since the sum is made up from individual vectors each with a phase and amplitude, the sum might occasionally become close to zero, creating a singularity characterised by loss of echo signal. When measuring tissue motion by analysis of phase variations, this becomes a problem. When the signal becomes close to zero, quite unpredictable phase variations might occur, causing lasting errors in the estimate of tissue position. This can be overcome by making multiple observations of phase variations from a range of locations, and computing an average phase difference weighted by the intensity of the signal.

The ultrasound beam from the transducer should be at a non-perpendicular angle ($\alpha$) to the motion vector of the internal structure, i.e. the cranio-caudal direction of the patient. Preferably the angle is below 60° and more preferably below 45°.

The method may further comprise determining one or more derived respiration properties from the motion, which may include a respiratory pattern, a breathing rate, a tidal volume, or a motion amplitude.

The technique above may be particularly applicable to patients receiving support from a mechanical ventilator. Thus, in various embodiments, the patient may be receiving support from a mechanical ventilator or is undergoing a spontaneous breathing trial for removal of support from a mechanical ventilator.

The method may comprise setting initial or on-going operational parameters of the mechanical ventilator, based on the monitored respiration.

The method may comprise synchronising the operation of the mechanical ventilator with the breathing of the patient, for example a frequency or phase of pressure assistance or a general pressure assistance provided by the mechanical ventilator, based on the monitored respiration. In one embodiment, the operation of the mechanical ventilator may be controlled so as to provide pressure assistance responsive to detecting patient contribution.

Where the patient is undergoing a spontaneous breathing trial, the method may comprise reducing or removing mechanical ventilation support for a period of time, such as 5 to 30 minutes or 0.5-30 minutes, and monitoring respiration during this time to determine a likelihood of a successful spontaneous breathing trial. The method may further comprise determining, in preferably less than the duration of the trial, e.g. less than 25 minutes, that a likelihood of the patient successfully completing the spontaneous breathing trial is below a predetermined threshold and returning mechanical ventilation support before unnecessary complication of the patient's condition.

In further embodiments, the patient may be a trauma patient, a cardiac arrest patient, a spinal cord injury patient, a pulmonary patient, such as a COPD patient, a post-operative patient, or a patient under the influence of analgetic drugs known to negatively affect respiration.

The present invention also provides an ultrasound apparatus for non-invasively monitoring respiration of a patient, the apparatus comprising: at least one ultrasound transducer element for placing on the patient to aim at an internal structure of the patient's body; and a controller for controlling the ultrasound transducer element and processing ultrasound signals; wherein the controller is arranged to transmit ultrasound into the body toward the internal structure of the patient's body; measure the phase of ultrasound echo signals received from the internal structure at multiple points along a depth range selectable by a user; the phase being measured for at least a first and a second echo signal, the first and second echo signals being received at different times; detect the motion of the internal structure within the patient's abdomen by reference to differences in the measured phase between the first and the second echo signals; and thereby monitor the respiration of the patient.

The apparatus is for use with internal structures including the liver, spleen and kidneys and thus is arranged to process ultrasound echo signals from those internal organs in order to monitor the respiration of the patient by associating movement of those organs with movement resulting from respiration. There may be a single ultrasound transducer element acting to both transmit and receive the ultrasound, or alternatively multiple ultrasound transducer elements may be used. The apparatus can include an input device allowing a user to select a depth range.

The controller may be arranged to carry out method steps as discussed above. For example, the motion of the internal structure may be calculated based on the measured phase at the multiple points along the depth range and the differences in phase for at least two echo signals received at different times by calculating the displacement of the tissue as an average along the ultrasound sound beam, where the observations of displacement at the multiple points along the depth range are weighted by their signal intensities before the averaged displacement is calculated.

The apparatus may comprise a contact layer to be positioned between the transducer and the skin. The contact layer might be made from an adhesive material. The contact layer comprise an ultrasound contact gel, a glue, or an adhesive tape material that allows transmission of ultrasound, such as the sonolucent silicone tape described in WO2011/135288. Gel, glue and tape might also be used in various combinations. The contact layer may comprise removing protective covers that may be removed to expose the adhesive before the surface is brought in contact with the body.

The surfaces of the apparatus adapted to be in contact with the patient's body are configured to provide conformal contact with the surface of the body.

The apparatus may include at least one power source for powering the parts of the apparatus.

The transducer may be connected either by wire or by (short-range) digital or analogue radio communication to the processing circuitry, which may provide signals from the target tissue. The processing circuitry may be partly or fully digital.

The apparatus may comprise a monitor that provides information about the measured motion of the tissue (or a respiratory property derived from the motion) to an observer (e.g. a physician or the patient). The processing circuitry and/or the monitor may provide for control of the measurements performed. Such control may include calculation of parameters related to measurements.

Preferably, the apparatus is a portable device adapted such that a patient can wear the device during normal life. This allows continuous monitoring outside of a hospital environment and with a non-invasive and safe technology.

As above, the apparatus (and preferably the processing circuitry of the apparatus) may determine a displacement of the internal structure obtained by any one of: integrating a velocity of the internal structure detected using the Doppler Effect; interferometry analysis of the phase of the reflected wave; mapping of ultrasound speckles within the internal structure; and determining displacement of one or more anatomical landmark.

The apparatus can advantageously be used in a mechanical ventilation system along with a mechanical ventilator, and thus the invention extends to such a system, wherein the mechanical ventilator is for providing support to a patient and the apparatus is for non-invasively monitoring the respiration of the patient during support via the mechanical ventilator.

The mechanical ventilation system may be arranged to synchronise the operation of the mechanical ventilator with the breathing of the patient based on the monitored respiration and/or to control the operation of the mechanical ventilator so as to provide pressure assistance responsive to detecting patient contribution. The system may be arranged to carry out a spontaneous breathing trial by reducing or removing mechanical ventilation support for a period of time and monitoring respiration during this time to determine a likelihood of a successful spontaneous breathing trial.

BRIEF DESCRIPTIONS OF THE DRAWINGS/FIGURES

Certain preferred embodiments of the present invention will now be described in greater detail, by way of example only and with reference to the drawings, in which.

The features and advantages of the present embodiments will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

A system and a method are disclosed for performing ultrasonic interferometry to produce at least one measurement of tissue structures in a living body, for acquisition of physiological signals. The data from these signals may be utilized for patient monitoring and other diagnostic purposes. Further embodiments may also allow for the monitoring of derived signals such as respiratory patterns, breathing rate, and a tidal volume, to name a few examples.

Since several internal organs, particularly those in the upper abdomen such as the liver, the spleen and the kidneys, move with respiration, their motions can be used to indirectly monitor respiration, i.e. without directly monitoring the lung or diaphragm. The liver, in particular, is a useful target. The liver is a large piece of tissue, allowing for placement of an ultrasound transducer on the skin surface without any need for precise anatomical guidance, and is easily accessible by ultrasound from the exterior of the body. The spleen is smaller than the liver, and can be hidden by gas pockets, but still presents a viable target. The kidneys again are smaller than the liver and are harder to access, but also move significantly with respiration.

Figure 1:
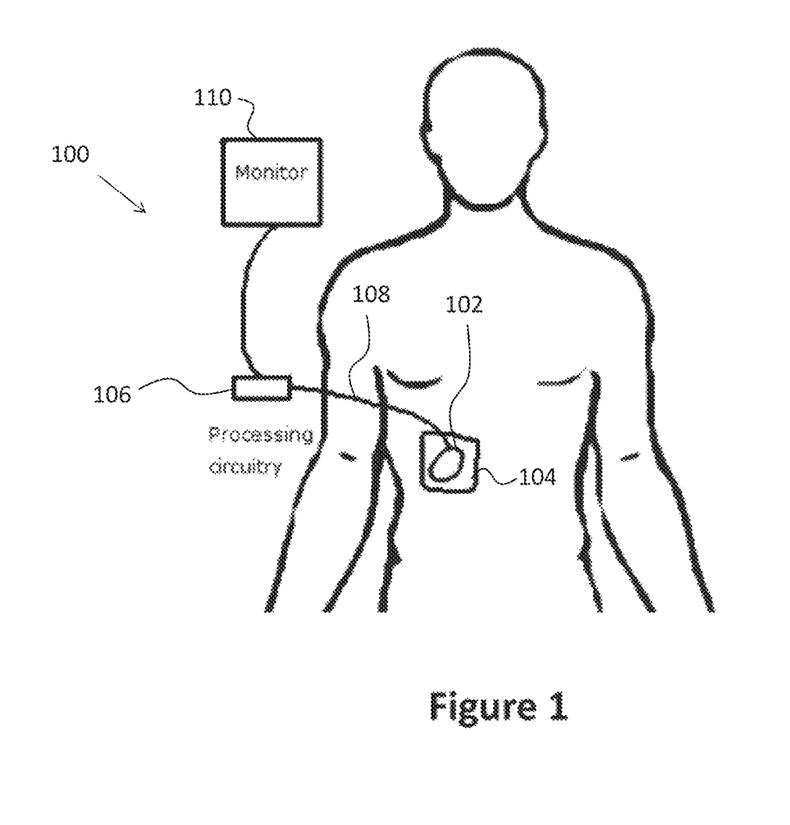
FIG. 1 shows a patient connected to a system for monitoring respiration, according to an embodiment.

FIG. 1 illustrates a respiration monitoring system 100, according to an embodiment. Monitoring system 100 includes a probe 102 having a contact layer 104 to attach probe 102 to the body of a patient being monitored. The patient may be a human or any other animal species. Monitoring system 100 also includes processing circuitry 106 and a communications interface 108 between processing circuit circuitry 106 and probe 102. A monitor 110 may also be included to display images or provide other information to a user or to the patient based on signals received from probe 102. Monitoring system 100 also includes at least one power source (not shown) for powering parts of the device, according to their requirements. Several of these parts may be integrated in a single device. For example, monitor 110 and processing circuitry 106 may be integrated into a single device.

Contact layer 104 may include an ultrasound contact gel, a glue or an adhesive tape material that allows transmission of ultrasound, such as the sonolucent silicone tape described in U.S. Patent Publication No. 2013/0165005, the disclosure of which is incorporated by reference herein. Gel, glue and tape might also be used together in various combinations. The surfaces in contact with the patient's body are configured to provide conformal contact with the surface of the body. A method of applying probe 102 to a living body using an adhesive tape might include removing protective covers to expose contact layer 104 before the surface is brought in contact with the body.

Communications interface 108 may represent a wire or any short-range digital or analog radio communication between probe 102 and processing circuitry 106. Communications interface 108 transits data received from probe 102 to processing circuitry 106 where the data is based on reflections of ultrasound signals from within the body of the patient. Communications interface 108 also transmits signals from processing circuitry 106 to probe 102 to cause the transducer within probe 102 to output ultrasound pulses. Processing circuitry 106 may be designed to process signals from probe 102 so as to derive a measurement of a motion of a target tissue of the patient. The processing performed by processing circuitry 106 can be partly or fully digital.

In some embodiments, monitoring system 100 can be made portable so that the patient can live normally while still being continuously monitored with a non-invasive and safe technology. That is to say, a system including at least probe 102 and processing circuitry 106 is of a suitable size and weight that it can be carried on the patient's body without impeding routine activates, and contact layer 104 includes an adhesive material that is sufficiently strong such that probe 102 remains in contact with the skin during such activities.

In some embodiments, monitoring system 100 includes monitor 110 that provides information about the measured motion parameters from the tissue to a human observer (e.g. a physician or the patient). Processing circuitry 106 and/or the monitor 110 may provide for control of the measurements being performed.

Figure 2:
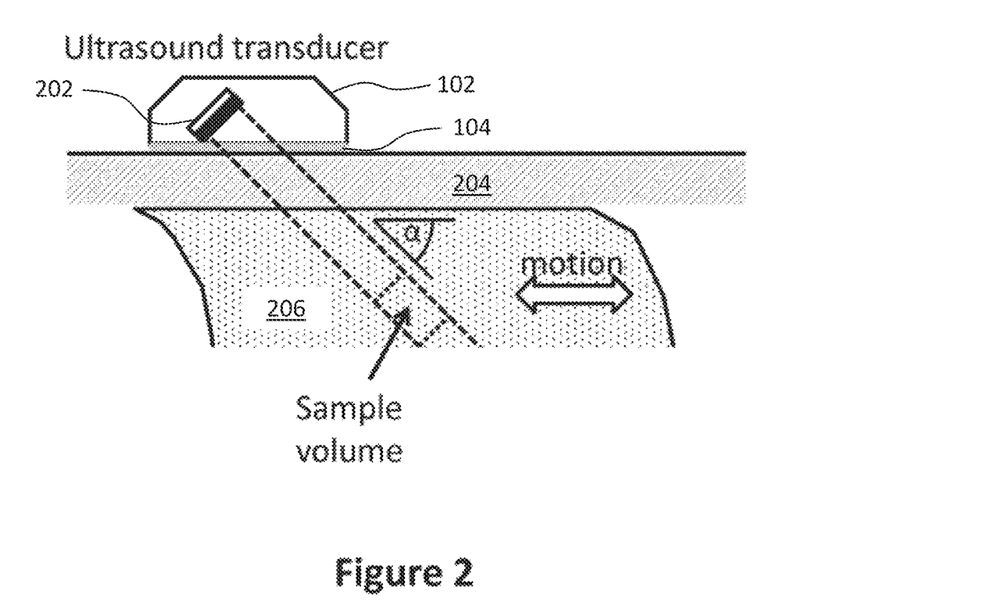
FIG. 2 shows a partial, vertical cross section through the patient illustrating an ultrasound transducer of the system, according to an embodiment.

FIG. 2 illustrates a close-up view of probe 102 having at least one ultrasound transducer 202, and being attached to the skin 204 of a patient using contact layer 104, according to an embodiment. Pulsed ultrasonic waves from at least one ultrasound transducer 202 are transmitted into the body, and the reflected echo signals are used to estimate a property of a target region (identified in FIG. 2 as "Sample volume"), based on one or more characteristics of the echo signals (e.g. phase shift between successive ultrasound pulses). The target region is provided at a given depth that is controllable as described further herein.

The sample volume may be a volume within an internal structure 206 that moves in response to respiration from the patient. Internal structure 206 may be an organ, bone, or connective tissue, to name a few examples. According to an embodiment, processing circuitry 106 calculates motion parameters, such as velocity, or other derived parameters, based on the motion pattern of internal structure 206.

The motion of the liver has been shown to closely follow the motion of the thoracic diaphragm muscle, and measurements of liver motion can, for this reason, be a good surrogate for direct measurements of diaphragm motion. Other organs may be used as well for this purpose, such as the kidney or the spleen.

According to an embodiment, Doppler-based techniques can be used for estimating the motion of tissue and fluids. Pulses of ultrasound are emitted into the tissue, and the echoes that are received from a pre-set depth, which is determined by an adjustable delay between emission of each pulse and a corresponding reception gate (see FIG. 3), are processed in order to detect and measure a shift in frequency related to tissue velocity. Integration of velocity over time will then give the displacement of the tissue. Since the phase of a signal at a given point in time is determined by the temporal integral of frequency in the past, phase variations of an echo signal may be used as a measure of tissue displacement. This technique (interferometry) is commonly used for accurate measurements of distances by counting of light wave cycles.

When a piece of tissue moves a distance (s), then the change in phase ($\Delta\varphi$) of an ultrasound echo received from the tissue is represented by:

$$\Delta\phi = 4\pi \frac{s}{\lambda} \cos(\alpha)$$

where $\lambda$ is the wavelength of the ultrasound, and a is the angle between the direction of the ultrasound beam and the motion vector (as illustrated in FIG. 2), e.g., the craniocaudal direction of the patient.

Since the wavelength depends on frequency ($f_0$) and speed of sound (c), the change in phase ($\Delta\varphi$) of an ultrasound echo received from the tissue may also be represented by:

$$\lambda = \frac{c}{f_0} \text{ and } \Delta\phi = 4\pi \frac{f_0 s}{c} \cos(\alpha)$$

Figure 3:
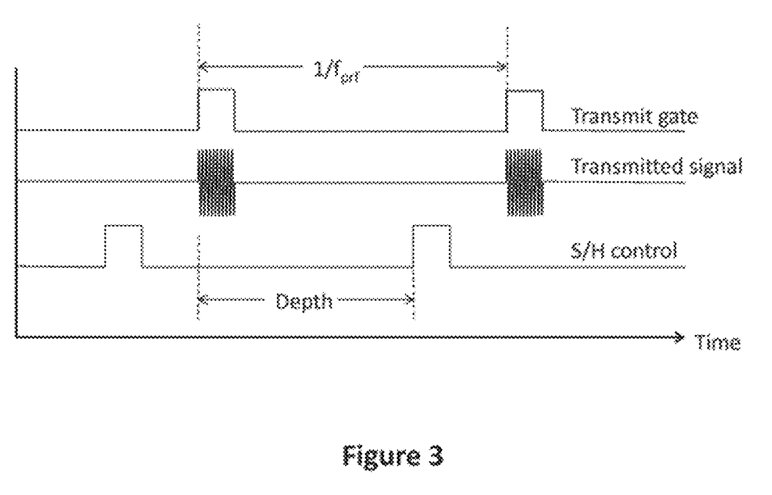
FIG. 3 shows exemplary input and output data for the ultrasound transducer.

With reference to FIG. 3, each ultrasound wavetrain that is emitted and received by transducer 202 will give one value for the echo signal phase. In order to keep track of phase changes, the maximum phase angle between two successive ultrasound echoes must be inside the interval from $-\pi$ to $\pi$ in order to be uniquely defined. The maximum distance of tissue motion between successive ultrasound pulses ($d_{max}$) may then be represented as:

$$d_{max} = \frac{\lambda}{4 \cos(\alpha)} = \frac{c}{4 f_0 \cos(\alpha)}$$

This establishes a relation between ultrasound frequency, the repetition frequency of pulse emissions ($f_{prf}$), speed of sound, sound beam angle and the maximum displacement of the tissue between pulses, and thus also the maximum tissue velocity ($V_{max}$) that can be observed as shown below.

$$V_{max} = \frac{c \cdot f_{prf}}{4 f_0 \cos(\alpha)}$$

Figure 4:
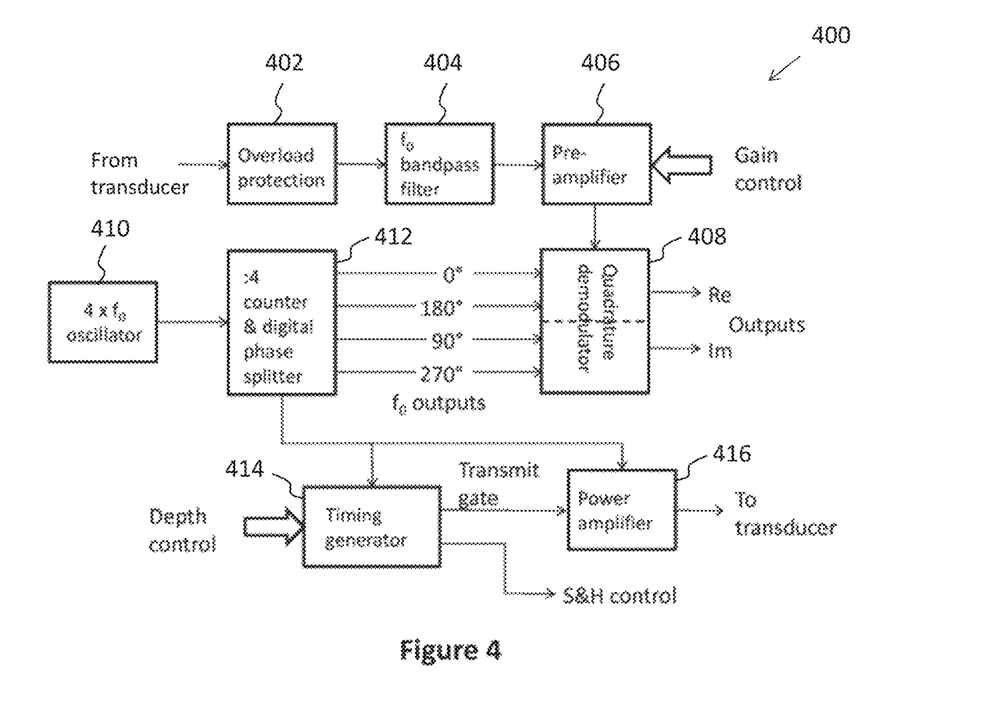
FIGS. 4 and 5 show schematic illustrations of processing circuitry and signal processing of the system, according to some embodiments.
Figure 5:
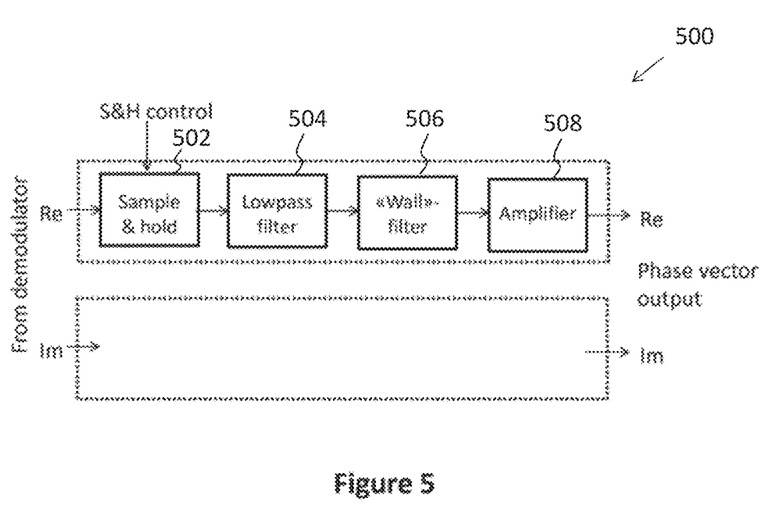

Processing circuitry 106 is schematically illustrated in FIGS. 4 and 5, according to some embodiments. Some example characteristics of processing circuitry 106 include:

Low Operating Frequency:

Scattering and reflection of ultrasound from red blood cells is very frequency dependent, and shows a strong increase at higher frequencies. The scattering properties of solid tissue do not have such pronounced frequency dependence. Thus, a lower frequency of operation might be preferred for recording of motion in solid tissues. A typical frequency range utilized for the ultrasound pulses is from 0.5 to 5 MHz, according to some embodiments.

Low Overall Gain:

The echoes from solid tissues are about 40-60 dB stronger then the echo from blood, and so the amplification of the returned echo and/or the emitted ultrasound intensity can be reduced correspondingly.

Filter Settings:

Example filter settings for recording of respiratory motion of the patient is in the range 0.01-0.1 Hz, depending on the operating frequency of the system. The filter settings may be used for removal of echoes from stationary tissue elements when recording the respiratory motion. The filter settings may be used to compensate for drift in electronic circuits and signal leakages between ultrasound transmit and receive circuits.

Large Sample Volume:

A large volume along the beam direction is preferred for recording of respiratory motion, preferably with a size in the range from 1 to 5 cm, corresponding to a reception gate duration of 13 to 65 ps, according to some embodiments.

Using a large depth volume will improve the amplitude stability of the signal and avoid drop-outs if the sample volume happens to be completely inside a vessel or a bile duct. A distance from ultrasonic transducer 202 to a center of the sample volume may be in a range from 5 to 15 cm, depending on the position of probe 102 on the body surface, and on the size of the body and size of internal structure 206, according to some embodiments. It might also be advantageous to use an unfocused, or only slightly focused ultrasound beam in order to increase the time of observation of individual scatter element in the tissue when motion is in a direction that deviates from the direction of the sound beam, and will improve the accuracy of the estimated motion and velocity.

Phase Tracking and Summation:

Processing circuitry 106 is arranged to calculate the phase of the returned echo signal from the selected depth, according to an embodiment. This calculation may be based on the Hilbert transform of the signal, or on synchronous demodulation of the signal giving a composite signal that represents both the real and imaginary part of the phase vector.

FIG. 4 illustrates an analog processing architecture 400 that may be used within processing circuitry 106, according to an embodiment. Analog processing architecture 400 is arranged to both process received signals from the transducer, and also to generate signal pulses that are transmitted to the transducer to become the ultrasound pulses. Analog processing architecture 400 receives signals from transducer 202 at an overload protection stage 402. Overload protection stage 402 includes circuitry designed to protect against the high voltage signals produced by a power amplifier 416 that are sent to transducer 202 to produce the transmitted ultrasound pulses. The various stages of analog processing architecture 400 downstream from overload protection stage 402 may be damaged by signals having a high voltage amplitude. Signals received from transducer 202 have a voltage amplitude in the uV range, while signals generated by power amplifier 416 to be sent to transducer 202 have a voltage amplitude between 20 and 50 volts, according to some embodiments.

Following overload protection stage 402, signals received from transducer 202 are filtered at bandbass filter stage 404 to reduce noise at frequencies far above and below the center frequency of the received signals. The center frequency of the signals received from transducer 202 may be in a range from about 2 MHz to about 4 MHz. For example, bandpass filter stage 404 may include a bandpass filter having a center frequency around 2 MHz with a bandwidth between 200 KHz and 500 KHz, when the center frequency of the signals received from transducer 202 is also about 2 MHz.

Following bandpass filter stage 404, the received signals are amplified at pre-amplifier stage 406, according to an embodiment. The gain of pre-amplification stage 406 may be controlled by user input, or automatically controlled by analog processing architecture 400. The gain is preferably high enough to accurately measure the received signal, but low enough to avoid clipping and oversaturation of the received signal.

The amplified signals received from transducer 202 are received by a demodulation stage 408, according to an embodiment. Demodulation stage 408 includes circuitry capable of multiplying the received signal with four reference signals having the same center frequency, but different phase. These four reference signals are produced by an oscillator 410, which generates a signal having a frequency of 4 times the center frequency. For example, for a received signal having a center frequency of about 2 MHz, oscillator 410 generates a signal having an 8 MHz center frequency. A phase splitting stage 412 receives the 8 MHz signal from oscillator 410 and generates the four reference signals, each at 2 MHz center frequency, and each offset by a phase difference of $\pi/2$.

Demodulator stage 408 multiplies the received signal with each of the reference signals to produce real and imaginary output signals. The real output signal is produced as a result of multiplication between the received signal and each of the reference signals having 0 degree and 180 degree phase offsets. The imaginary output signal is produced as a result of multiplication between the received signal and each of the reference signals having 90 degree and 270 degree phase offsets.

Phase splitting stage 412 also generates a fifth signal having a same center frequency as the received signal from transducer 202 (e.g., around 2 MHz.) This fifth signal is received by a timing generator stage 414 and also by power amplifier stage 416. Timing generator stage 414 is designed to provide a delay between signal pulses to be sent to transducer 202 and the gating of echo reception between emissions in order to define a desired depth range along the ultrasound beam direction. This delay may be determined based on a depth control parameter set by a user or set automatically by processing circuitry 106. Power amplifier stage 416 receives the fifth signal, e.g. at 2 MHz, generated by splitting stage 412 and amplifies the signal to have a voltage amplitude anywhere between 20 V and 50 V to be sent to transducer 202. This high-voltage signal drives transducer 202 to create the ultrasound pulses sent into the body.

FIG. 5 illustrates a conditioning circuit 500 designed to receive the demodulated real and imaginary component outputs from demodulator 408 shown in FIG. 4, according to an embodiment. Conditioning circuit 500 may be considered part of analog processing architecture 400. The real component of the output is received by a gating circuit 502, that may be arranged to perform a sample and hold function for determining the desired depth range. Circuit 502 receives the delay time between transmitted pulses from timing generator stage 414 and uses this delay time to correspondingly sample the real component of the output only when the echo signal is received, according to an embodiment. A signal processing path is also provided for the imaginary part of the signal, which may be identical to the processing path used for the real part of the signal. The signal is then passed through a series of filter and/or amplifier stages to achieve a phase vector output that can be compared to previously measured phase vectors to determine characteristics about the tissue or region being examined. For example, the filter stages may include a low pass filter stage 504 to reduce high frequency noise and a wall filter stage 506 to reduce high amplitude, low velocity signals that result from unwanted reflections from vessel walls. The amplifier stage 508 may be used to further amplify low voltage signals for better analysis.

The measured phase vectors from the previous echo reception may be be stored in memory (not shown) for later comparison with new measured phase vectors. In some embodiments, only a single previously measured phase vector is stored in memory at any given time.

Figure 6:
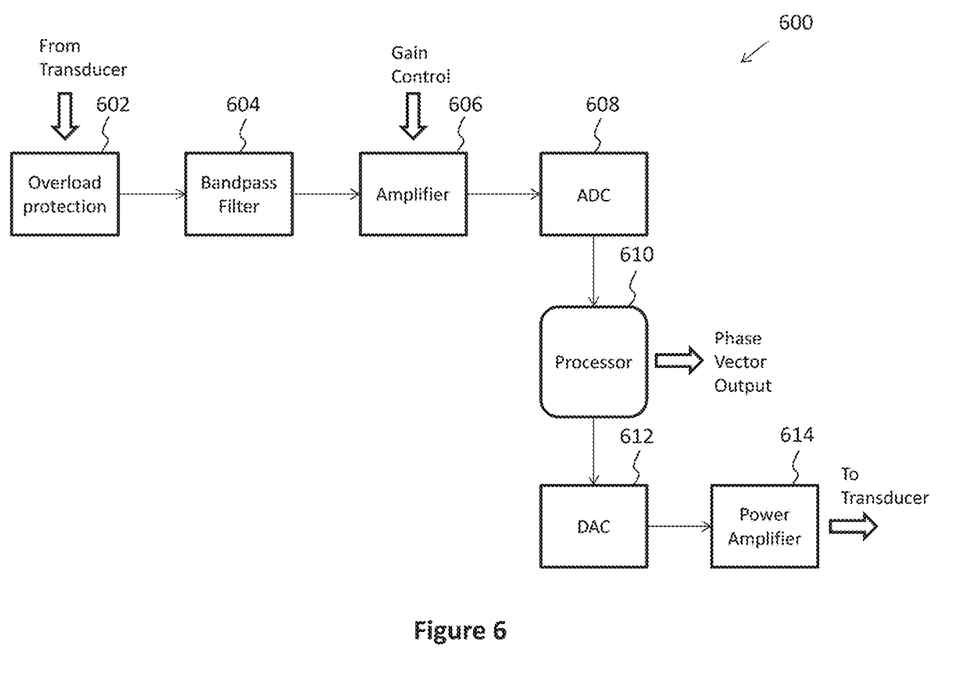
FIG. 6 shows another schematic illustration of processing circuitry, according to an embodiment.

FIG. 6 illustrates a digital processing architecture 600 that is an alternative design to analog processing architecture 400 and may be used within processing circuitry 106, according to an embodiment. Similar to the embodiment of FIG. 4, digital processing architecture 600 includes an overload protection stage 602, a bandpass filter stage 604 and a pre-amplifier stage 606 to receive a signal from transducer 202. As such, these stages are not described again here. After the analog signal has been filtered and amplified, it is converted into a digital signal by an analog-to-digital converter (ADC) 608. The digital signal is then received by processor 610.

According to an embodiment, processor 610 digitally performs all of the functions of blocks 408, 410, 412, and 414 from analog processing architecture 400. Thus, processor 610 generates a complex signal (containing real and imaginary components) based on the multiplication of the received digitized signal from transducer 202 with self-generated reference signals at different phase offsets from the received signal. Processor 610 also controls the timing of the output pulses to be sent to transducer 202. The signals to be sent to transducer 202 are first converted back to analog signals using a digital-to-analog converter (DAC) 612 before being amplified using power amplifier 614. Power amplifier 614 works in the same way as power amplifier 416 from analog processing architecture 400.

Processor 610 may be designed to perform a gating operation on the generated complex signal to only process those signals that align with the received echo pulses from transducer 202. Processor 610 also performs both low and high pass filtering on the generated complex signal to ultimately produce the phase vector output. As discussed with respect to analog processing architecture 400, the phase vector may be stored (e.g., in memory or a register) and compared with a previous stored phase vector to determine tissue characteristics.

From a series of phase vectors obtained as described above, the tissue displacement is calculated as a cumulative sum of phase differences. If P is a series of phase vectors obtained from successive ultrasound pulse emissions and receptions (numbered by p), then the cumulated phase shift ($\phi_{cum}$) caused by the total displacement at sample number n becomes:

$$\phi_{cum} = \sum_{p=1}^{n} \Delta\phi = \sum_{p=1}^{n} \arg(P_p \overline{P_{p-1}})$$

The tissue displacement (S) can then be calculated as:

$$S = \frac{\lambda \phi_{cum}}{4\pi \cos(\alpha)}$$

Cumulated phase and tissue displacement can also be calculated from the pattern of sign variations of the complex vector describing the phase of the echo. This might be implemented as an up/down counter circuit controlled by two bits of information derived from the sign of the real and imaginary parts of the phase vector.

The counter should be incremented each time the vector enters a new quadrant in counter clockwise order, and decremented when a new quadrant is entered in clockwise order. This scheme can be implemented by only requiring a slow two-bit digital interface between analogue and digital circuits, leading itself to a simple low-power implementation. From the count number (N), tissue displacement can be calculated as:

$$S = \frac{N\lambda}{8 \cos(\alpha)}$$

The liver and the spleen move quite uniformly and linearly with respiration. Thus, as discussed above, when an ultrasonic beam is aimed towards one of these tissues, about the same velocities will be observed over a wide range of distances into the tissue along the ultrasound beam direction. This is in contrast to measurements of blood flow with Doppler techniques, where a considerable variation in fluid velocity is expected along the direction of the beam.

It is reasonable to assume that the robustness and accuracy of estimates of phase shifts in the ultrasound echo caused by solid tissue motion can be improved by averaging of observations of phase from several locations along the ultrasound beam.

Solid tissues, such as the liver, have structural irregularities that scatter ultrasound. The echo received from the tissue will be a sum of individual contributions from such scattering elements. Since the sum is made up from individual vectors each with a phase and amplitude, the sum might occasionally become close to zero, creating a singularity characterised by loss of echo signal. When measuring tissue motion by analysis of phase variations, this becomes a problem. When the signal becomes close to zero, quite unpredictable phase variations might occur, causing lasting errors in the estimate of tissue position.

This can be overcome by making multiple or continuous observations of phase variations from a range of locations (depths) along the sound beam, and computing an average phase difference ($\Delta\varphi$) weighted by the intensity of the signal, and then processing these phase values further to give tissue velocity and displacement as described above, according to an embodiment. Since the intensity at a given location along the beam might change from one pulse of ultrasound to the next due to tissue motion, the intensity of both the current and the previous ultrasound echo from that location may be considered when performing the calculation of the intensity-weighted phase.

According to an embodiment, the received echo from two successive pulses of ultrasound (numbered as n and n+1) is complex-demodulated to give two sampled time series of the complex echo signal ($P_n(t)$ and $P_{n+1}(t)$) as a function of time or depth into the tissue. The range of (t) is set to cover the distance along the sound beam that will be used for the calculations. In order to calculate the phase difference, the product of $P_{n+1}$ and the complex conjugate of $P_n$ is calculated:

$$Q(t) = \overline{P_n(t)} P_{n+1}(t)$$

The phase contained in Q will now be the phase difference between $P_{n+1}$ and $P_n$ as a function of time (and distance) and the absolute value of Q will be the product of the echo amplitudes from $P_{n+1}$ and $P_n$ which is a suitable factor for weighting in the process of calculation of an average phase value. Calculation of the weighted phase difference between $P_{n+1}$ and $P_n$ can now be done by simple summation of the elements in Q and calculating the phase angle of the sum:

$$\Delta\phi = \arg(\Sigma Q)$$

This is repeated for successive pairs of received echo signals ($P_{n+1}$ and $P_{n+2}$, $P_{n+2}$ and $P_{n+3}$, $P_{n+3}$ and $P_{n+4}$, etc.) to calculate the cumulated phase shift and motion of the tissue over a longer time period.

Several parameters (with suggested ranges shown in parentheses) that determine the performance of the method can be optimised, such as the emitted frequency (e.g. 1-10 MHz), the duration of the emitted wavetrain (e.g. 0.5-100 µs), the bandwidth of the synchronous demodulator (e.g. 10 kHz-2 MHz) and the length of the depth range within the organ to use for the calculations (e.g. 0.5-10 cm).

The method increases the robustness in situations where the beam accidentally traverses regions within the liver that are fluid filled, such as vessels, bile ducts or cysts. The fluid within these structures gives echoes that are far weaker than echoes from the surrounding solid tissue (e.g., by −40 dB or more), and might cause an apparent loss of signal if the measurement sample volume happens to be located inside such a structure. As the tissue moves back and forth at an angle with respect to the sound beam, this is likely to occur. With the intensity-weighted phase calculation method described above, this problem will be eliminated since data is collected over a larger distance along the beam, such that at least some part of solid tissue contributes to the signal.

As will be appreciated, the apparatus above provides a measurement of the motion of an internal structure within the patient's abdomen, such as solid tissue like the liver or spleen, which closely follows movement of the diaphragm. This can be used for any application where monitoring respiration is necessary, and may replace, or be used in combination with known devices such as respiratory belts, flowmeters, spirometers, nasal temperature sensors, pressure transducers and radar systems.

The technique may, however, also be used to monitor breathing of a patient for other applications. For example, characterization of pulmonary function might be performed by extracting information and patterns of respiratory motion that might be interpreted as a substitute for spirometry values.

Another medical application for this invention is to monitor patients on mechanical ventilation and help in the synchronization between the ventilator and the patient. A further use is to monitor the motion when the patient is decoupled from the ventilator to characterize the thoracic diaphragm movements and to determine as early as possible whether the patient can be successfully weaned from mechanical ventilation or not. It can also be used in follow up of the patients.

During or when initiating mechanical ventilation, the technique for monitoring of respiration can be used to guide the mechanical ventilation pressure and/or CPAP (continuous positive airway pressure) settings. When inhalation pressure is increased, the lungs will initially expand, and then their volume will reach a plateau where further pressure increase will not improve ventilation, and possibly cause harm. This might be avoided by monitoring the gradual downward displacement of the organs in the upper abdomen.

The method might also be used for monitoring patients that are on mechanical ventilation support, with the purpose of detecting the patient's own breathing efforts. Such efforts might indicate that the ventilator settings are incorrect, or that the patient is insufficiently sedated.

This technique may also be used to synchronize the operation of the mechanical ventilator with the breathing efforts of the patient, for example by adjusting the frequency or phase of the mechanical ventilator's pressure assistance in order to match the patient's needs and to increase the patient's comfort. This can reduce asynchrony between mechanical ventilator action and the patient's own breathing action, e.g. where the patient's effort (e.g. diaphragm movement) is out of sync with the mechanical ventilator, or where the patient's effort starts before the mechanical ventilator initiates pressure support resulting in the patient receiving no air.

The method might detect the initial contraction of the diaphragm, and use this for triggering and synchronizing the ventilator. This will enable normal chemoreceptor control of ventilation, while reducing the efforts and fatigue associated with the work of breathing. For example, when the patient makes an effort to breathe (e.g. diaphragm movement is detected) the mechanical ventilator may provide pressure support in response.

In order to determine whether a patient is ready to be removed from ventilator support, a spontaneous breathing trial (SBT) is carried out. During an SBT, the mechanical ventilator is disabled for 30 minutes, although other disablement time periods could be selected. If the patient is able to successfully breathe for 30 minutes, then they are taken off of the ventilator. If not, then ventilator support is returned. Ventilators are expensive to operate, and so it is desirable to remove ventilator support from patients as soon as possible. However, removing support too early can be detrimental to a patient's recovery, resulting in a prolonged need for ventilation support. It is now well known that diaphragm weakness is associated with a poorer prognosis.

The technique for monitoring respiration can be used to aid in assessing readiness for a spontaneous breathing trial (SBT). To assess SBT readiness the mechanical ventilator may be removed for a short period of time, such as 10 cycles, and diaphragm displacement can be monitored (amplitude, slope and regularity) to predict the success or failure of a 30 minutes SBT.

The technique can also be used to monitor respiration during the SBT. The development of diaphragm displacement (amplitude, slope and regularity) can be monitored during the trial to predict success or failure before the end of the trial, helping to reduce the risk of harm being caused in patients who are unlikely to succeed.

A further use may be for patients requiring respiratory rehabilitation where the movement of the diaphragm is crucial. The patients may be trauma patients, cardiac arrest patients, spinal cord injury patients, pulmonary patients such as COPD (chronic obstructive pulmonary disease) patients or ARDS (Acute respiratory distress syndrome) patients. The technique may also be used in post-operative patient monitoring. The respiration can be monitored to see development of diaphragm displacement (amplitude, slope and regularity) to give early warning if respiration halts.

In another embodiment, the technique above may be used during a CT guided puncture operation. However, it will be understood that, as discussed above, embodiments of the invention can also be used in any other area requiring respiration monitoring, such as the fields of radiation therapy or mechanical ventilation.

The ultrasound transducer may be positioned on the patient and directed towards the liver prior to the patient being given a CT or MRI scan. The transducer emits a series of ultrasound pulses and detects their echoes in the known manner. Based on the detected echoes, movement of the liver can be detected, and hence the position of the diaphragm can be determined.

After the patient has been fitted with the transducer, a CT or an MRI scan may be performed on the patient to determine the precise location of the target (e.g. a lesion to be punctured). During the scan, the patient is required to hold his breath so that a clear image is produced with the lungs in one position. While the scan is being performed and while the patient is holding his or her breath, the exact position of the diaphragm is presented on the monitor and the position-value is noted.

The image from the scan may be used to calculate the depth and angle at which a needle must be inserted for the lesion to be punctured. When the operator is ready to perform the puncture, the patient is asked to inhale until the display indicates that the diaphragm is in the same position as it was when the scan was performed. If the patient inhales too much and the transducer indicates that the level of inspiration is greater than that held during the scan, the operator can instruct the patient to exhale a little. If necessary, the patient can relax and inhale again until the operator is happy with the position of the diaphragm.

In this way, the operator can be sure that the lesion is at the same position within the patient as it is shown in the CT or MR image while he or she performs the puncture. In the case of CT, the location of the needle may, however, still be checked by means of a further scan.

As described above, the apparatus of the present invention can also be used to improve radiotherapy treatments by reducing the area that needs to be irradiated. The basic procedure described above is employed, however, the embodiment is modified to provide a control output from the processor for controlling a source of radiation.

After the location of the tumor within the patient has been determined from the scan image, a radiation source is aimed at that location. This is connected to the control output such that the radiation source only emits when triggered to do so by the output signal from the processor.

The patient is allowed to breathe continuously throughout the radiation treatment. Meanwhile, the processor uses the outputs from the transducer array to continuously monitor the position of the diaphragm. When its position corresponds to the position that was determined during the scan, the processor sends a signal to trigger the radiation source to irradiate the target area of the patient. Thus, the area of the patient that needs to be irradiated can be significantly reduced because the location of the target can be determined to a much greater accuracy.

The output of the apparatus may be in the form of diaphragm position, amplitude of breathing motion, frequency (respiratory rate) and/or velocity. Successive measurements performed on a single patient or a population may yield a historical trend allowing progress or deterioration of lung function to be monitored.

Figure 7:
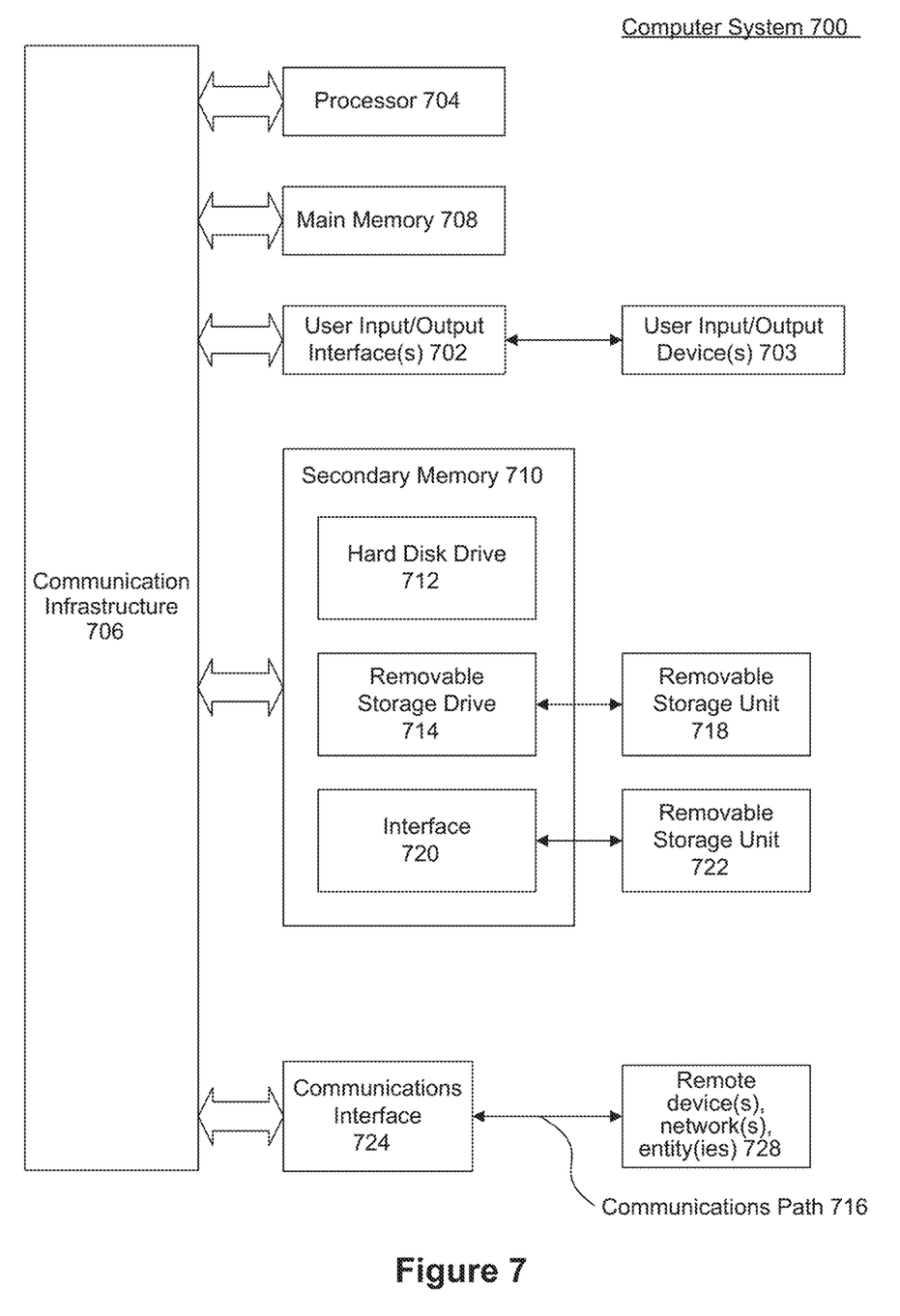
FIG. 7 shows an example computer system useful for implementing various embodiments.

Various embodiments described thus far can be implemented, for example, using one or more well-known computer systems, such as computer system 700 shown in FIG. 7. In an embodiment, computer system 700 may be programmed to implement one or both of processing circuitry 106 and monitor 110 illustrated in FIG. 1.

Computer system 700 includes one or more processors (also called central processing units, or CPUs), such as a processor 704. Processor 704 is connected to a communication infrastructure or bus 706. In one embodiment, processor 704 represents a field programmable gate array (FPGA). In another example, processor 704 is a digital signal processor (DSP).

One or more processors 704 may each be a graphics processing unit (GPU). In an embodiment, a GPU is a processor that is a specialized electronic circuit designed to rapidly process mathematically intensive applications on electronic devices. The GPU may have a highly parallel structure that is efficient for parallel processing of large blocks of data, such as mathematically intensive data common to computer graphics applications, images and videos.

Computer system 700 also includes user input/output device(s) 703, such as monitors, keyboards, pointing devices, etc., which communicate with communication infrastructure 706 through user input/output interface(s) 702.

Computer system 700 also includes a main or primary memory 708, such as random access memory (RAM). Main memory 708 may include one or more levels of cache. Main memory 708 has stored therein control logic (i.e., computer software) and/or data.

Computer system 700 may also include one or more secondary storage devices or memory 710. Secondary memory 710 may include, for example, a hard disk drive 712 and/or a removable storage device or drive 714. Removable storage drive 714 may be a floppy disk drive, a magnetic tape drive, a compact disc drive, an optical storage device, tape backup device, and/or any other storage device/drive.

Removable storage drive 714 may interact with a removable storage unit 718. Removable storage unit 718 includes a computer usable or readable storage device having stored thereon computer software (control logic) and/or data. Removable storage unit 718 may be a floppy disk, magnetic tape, compact disc, Digital Versatile Disc (DVD), optical storage disk, and/any other computer data storage device. Removable storage drive 714 reads from and/or writes to removable storage unit 718 in a well-known manner.

Secondary memory 710 may include other means, instrumentalities, or approaches for allowing computer programs and/or other instructions and/or data to be accessed by computer system 700. Such means, instrumentalities or other approaches may include, for example, a removable storage unit 722 and an interface 720. Examples of the removable storage unit 722 and the interface 720 may include a program cartridge and cartridge interface (such as that found in video game devices), a removable memory chip (such as an EPROM or PROM) and associated socket, a memory stick and universal serial bus (USB) port, a memory card and associated memory card slot, and/or any other removable storage unit and associated interface.

Computer system 700 may further include a communication or network interface 724. Communication interface 724 enables computer system 700 to communicate and interact with any combination of remote devices, remote networks, remote entities, etc. (individually and collectively referenced by reference number 728). For example, communication interface 724 may allow computer system 700 to communicate with remote devices 728 over communications path 726, which may be wired and/or wireless, and which may include any combination of local area networks (LANs), wide area networks (WANs), the Internet, etc. Control logic and/or data may be transmitted to and from computer system 700 via communication path 726.

In an embodiment, a tangible apparatus or article of manufacture comprising a tangible computer useable or readable medium having control logic (software) stored thereon is also referred to herein as a computer program product or program storage device. This includes, but is not limited to, computer system 700, main memory 708, secondary memory 710, and removable storage units 718 and 722, as well as tangible articles of manufacture embodying any combination of the foregoing. Such control logic, when executed by one or more data processing devices (such as computer system 700), causes such data processing devices to operate as described herein.

Based on the teachings contained in this disclosure, it will be apparent to persons skilled in the relevant art(s) how to make and use the invention using data processing devices, computer systems and/or computer architectures other than that shown in FIG. 7. In particular, embodiments may operate with software, hardware, and/or operating system implementations other than those described herein.

Whilst a preferred embodiment of the present invention has been described, it will be appreciated that numerous variations of the system are within the scope of the invention. For example, in various embodiments, the apparatus may be composed of several transducers placed at different locations on the patient's body. The apparatus may also include additional sensors of different types, such as pulse oximeters, electrocardiographic electrodes, electromyographic electrodes, electrodermal activity sensors, or accelerometers, for simultaneous or complementary measurements.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of non-invasively monitoring the respiration of a patient using ultrasonic waves directed onto the body of the patient, the method comprising:
   coupling an ultrasonic transducer via a contact layer to the patient's body;
   selecting a depth range and a beam angle from the ultrasonic transducer to a sample volume within at least a portion of an internal structure inside the patient's body, the beam angle being a non-perpendicular angle between an ultrasound beam direction and a motion vector of the internal structure, the depth range comprising multiple points in the internal structure along the ultrasound beam direction, and the internal structure comprising one of a liver, a spleen, or a kidney of the patient;
   emitting a series of ultrasound pulses from the ultrasonic transducer into the patient's body towards the sample volume at the beam angle and detecting echoes of the emitted ultrasound pulses along the depth range;
   measuring phase values of at least first and second echo signals received from the internal structure at the multiple points along the depth range, the at least first and second echo signals being received at different times;
   detecting motion of the internal structure by calculating differences in the measured phase values of the at least first and second echo signals at the multiple points inside the sample volume along the depth range and calculating average phase values of the calculated differences in the measured phase values of the at least first and second echo signals; and
   associating the motion of the internal structure with movement caused by respiration to monitor or determine respiration parameters of the patient.

2. The method of claim 1, wherein the selected depth range as measured from the ultrasonic transducer to a center of the sample volume is between 5 cm to 15 cm.

3. The method of claim 1, wherein a size of the sample volume along the ultrasound beam direction is in a range from 1 cm to 5 cm.

4. The method of claim 1, wherein the at least first and second echo signals are a successive pair of echo signals.

5. The method of claim 1, wherein the at least first and second echo signals are complex-demodulated to give two sampled time series of complex echo signals as a function of time or depth into tissue of the internal structure, wherein a time range is set to cover a distance along the ultrasound beam direction to be used for the calculations, wherein a phase difference $$Q(t) = \overline{P_n(t)} P_{n+1}(t)$$

is calculated, wherein n and n+1 are related to numbers of received echo from successive ultrasound pulses, and t is related to the time of the distance along the ultrasound beam direction into the internal structure, and wherein a phase contained in Q(t) is a phase difference between complex echo signals Pn+1 and Pn as a function of time and distance, and an absolute value of Q(t) is a product of echo amplitudes of Pn+1(t) and a complex conjugate of Pn(t).

6. The method of claim 5, wherein calculation of a weighted phase difference between Pn+1(t) and Pn(t) is performed by summation of the elements in Q and calculating a phase angle (ΔΦ) of the sum:

$$\Delta\phi = \arg(\Sigma Q).$$

7. The method of claim 1, wherein interferometry is used to determine a phase of a given echo signal and the method further comprises cumulatively summing a phase shift between ultrasound measurements at different depths to determine a displacement of the internal structure.

8. The method of claim 1, comprising determining a phase shift caused by motion at two or more locations within the internal structure and determining an average phase shift to determine the motion.

9. The method of claim 8, wherein the average phase shift is an intensity-weighted average of multiple phase shift measurements.

10. The method of claim 1, wherein the non-perpendicular angle is below 60°.

11. The method of claim 1, wherein the non-perpendicular angle is below 45°.

12. The method of claim 1, wherein the respiration parameters comprise one or more of a respiratory pattern, a breathing rate, a tidal volume, a diaphragm displacement, a motion amplitude, a velocity of inspiration, a velocity of expiration, a peak value of velocity of inspiration, or a peak value of velocity of expiration.

13. The method of claim 1, wherein the motion vector of the internal structure is in a cranio-caudal direction of the patient.

14. A method of non-invasively monitoring the respiration of a patient using ultrasonic waves directed onto the body of the patient, the method comprising:
 coupling an ultrasonic transducer via a contact layer to the patient's body;
 selecting a depth range and a beam angle from the ultrasonic transducer to a sample volume within at least a portion of an internal structure inside the patient's body, the internal structure being one of a liver, spleen, or kidney of the patient, and the beam angle being a non-perpendicular angle between an ultrasound beam direction and a motion vector of the internal structure in a cranio-caudal direction of the patient, the depth range comprising multiple points in the internal structure along the ultrasound beam direction;
 emitting a series of ultrasound pulses from the ultrasonic transducer into the patient's body towards the sample volume at the beam angle and detecting echoes of the emitted ultrasound pulses along the depth range;
 measuring phase values of at least first and second echo signals received from the internal structure at the multiple points along the depth range, the at least first and second echo signals being received at different times;
 detecting motion of the internal structure by reference to a difference between the measured phase values of the at least first and second echo signals, the at least first and second echo signals being a successive pair of echo signals;
 determining a phase shift caused by motion at two or more locations within the internal structure and determining an average phase shift to determine the motion by calculating differences in the measured phase values of the at least first and second echo signals at the multiple points inside the sample volume along the depth range and calculating average phase values of the calculated differences in the measured phase values of the at least first and second echo signals; and
 associating the motion of the internal structure with movement caused by respiration to monitor or determine respiration parameters of the patient.

15. The method as claimed in claim 14, wherein the selected depth range as measured from the ultrasonic transducer to a center of the sample volume is between 5 cm to 15 cm.

16. The method as claimed in claim 14, wherein a size of the sample volume along the ultrasound beam direction is in a range from 1 cm to 5 cm.

17. The method as claimed in claim 14, wherein the at least first and second echo signals are complex-demodulated to give two sampled time series of complex echo signals as a function of time or depth into tissue of the internal structure, wherein a time range is set to cover a distance along the ultrasound beam direction to be used for the calculations, wherein a phase difference $$Q(t)=\overline{P_n(t)}P_{n+1}(t)$$

is calculated, wherein n and n+1 are related to numbers of received echo from successive ultrasound pulses, and t is related to the time of the distance along the ultrasound beam direction into the internal structure, and wherein a phase contained in Q(t) is a phase difference between complex echo signals $P_{n+1}$ and $P_n$ as a function of time and distance, and an absolute value of Q(t) is a product of echo amplitudes of $P_{n+1}(t)$ and a complex conjugate of $P_n(t)$.

18. The method as claimed in claim 17, wherein calculation of a weighted phase difference between $P_{n+1}(t)$ and $P_n(t)$ is performed by summation of the elements in Q and calculating a phase angle ($\Delta\Phi$) of the sum:

$$\Delta\phi=\arg(\Sigma Q).$$

19. The method as claimed in claim 14, wherein interferometry is used to determine a phase of a given echo signal and the method further comprises cumulatively summing a phase shift between ultrasound measurements at different depths to determine a displacement of the internal structure.

20. The method as claimed in claim 14, wherein the average phase shift is an intensity-weighted average of multiple phase shift measurements.

21. The method as claimed in claim 14, wherein the non-perpendicular angle is below 60°.

22. The method as claimed in claim 14, wherein the non-perpendicular angle is below 45°.

23. The method as claimed in claim 14, wherein the respiration parameters comprise one or more of a respiratory pattern, a breathing rate, a tidal volume, and a diaphragm displacement, a motion amplitude, a velocity of inspiration, a velocity of expiration, a peak value of velocity of respiration, or a peak value of velocity of expiration.

24. A method of non-invasively monitoring the respiration of a patient using ultrasonic waves directed onto the body of the patient, the method comprising:
 coupling an ultrasonic transducer via a contact layer to the patient's body;
 selecting a depth range and a beam angle from the ultrasonic transducer to a sample volume within at least a portion of an internal structure inside the patient's body, the internal structure being one of a liver, spleen, or kidney of the patient, and the beam angle being a non-perpendicular angle between an ultrasound beam direction and a motion vector of the internal structure in a cranio-caudal direction of the patient, the depth range comprising multiple points in the internal structure along the ultrasound beam direction;
 emitting a series of ultrasound pulses from the ultrasonic transducer into the patient's body towards the sample volume at the beam angle and detecting echoes of the emitted ultrasound pulses along the depth range;
 measuring phase values of at least first and second echo signals received from the internal structure at the multiple points along the depth range, the at least first and second echo signals being received at different times;
 detecting motion of the internal structure by calculating differences in the measured phase values of the at least first and second echo signals at the multiple points inside the sample volume along the depth range and calculating average phase values of the calculated differences in the measured phase values of the at least first and second echo signals, the at least first and second echo signals being a successive pair of echo signals; and
 associating the motion of the internal structure with movement caused by respiration to monitor or determine respiration parameters of the patient.

25. The method as claimed in claim 24, wherein the selected depth range as measured from the ultrasonic transducer to a center of the sample volume is between 5 cm to 15 cm.

26. The method as claimed in claim 24, wherein a size of the sample volume along the ultrasound beam direction is in a range from 1 cm to 5 cm.

27. The method as claimed in claim 24, wherein the at least first and second echo signals are complex-demodulated to give two sampled time series of complex echo signals as a function of time or depth into tissue of the internal structure, wherein a time range is set to cover a distance along the ultrasound beam direction to be used for the calculations, wherein a phase difference $$Q(t) = \overline{P_n(t)} P_{n+1}(t)$$

is calculated, wherein n and n+1 are related to numbers of received echo from successive ultrasound pulses, and t is related to the time of the distance along the ultrasound beam direction into the internal structure, wherein a phase contained in Q(t) is a phase difference between complex echo signals $P_{n+1}$ and $P_n$ as a function of time and distance, and an absolute value of Q(t) is a product of echo amplitudes of $P_{n+1}(t)$ and a complex conjugate of $P_n(t)$, and wherein calculation of a weighted phase difference between $P_{n+1}(t)$ and $P_n(t)$ is performed by summation of the elements in Q and calculating a phase angle ($\Delta\Phi$) of the sum:

$$\Delta\phi = \arg(\Sigma Q).$$

28. The method as claimed in claim 24, wherein interferometry is used to determine a phase of a given echo signal and the method further comprises cumulatively summing a phase shift between ultrasound measurements at different depths to determine a displacement of the internal structure.

29. The method as claimed in claim 24, comprising determining a phase shift caused by motion at two or more locations within the internal structure and determining an average phase shift to determine the motion.

30. The method as claimed in claim 29, wherein the average phase shift is an intensity-weighted average of multiple phase shift measurements.

31. The method as claimed in claim 24, wherein the non-perpendicular angle is below 60°.

32. The method as claimed in claim 24, wherein the non-perpendicular angle is below 45°.

33. The method as claimed in claim 24, wherein the respiration parameters comprise one or more of a respiratory pattern, a breathing rate, a tidal volume, and a diaphragm displacement, a motion amplitude, a velocity of inspiration, a velocity of expiration, a peak value of velocity of respiration, or a peak value of velocity of expiration.

* * * * *